United States Patent
Zvikhachevskaya et al.

(10) Patent No.: US 9,494,555 B2
(45) Date of Patent: Nov. 15, 2016

(54) SYSTEM AND METHOD FOR MEASURING AN ANALYTE IN A SAMPLE AND CALCULATING GLUCOSE RESULTS TO ACCOUNT FOR PHYSICAL CHARACTERISTICS OF THE SAMPLE

(71) Applicants: Anna Zvikhachevskaya, Iverness (GB); Stephen Mackintosh, Iverness (GB); Adam Craggs, Iverness (GB)

(72) Inventors: Anna Zvikhachevskaya, Iverness (GB); Stephen Mackintosh, Iverness (GB); Adam Craggs, Iverness (GB)

(73) Assignee: Cilag GmbH International, Zug (CH)

( * ) Notice: Subject to any disclaimer, the term of this patent is extended or adjusted under 35 U.S.C. 154(b) by 701 days.

(21) Appl. No.: 13/625,861

(22) Filed: Sep. 24, 2012

(65) Prior Publication Data
US 2014/0083868 A1 Mar. 27, 2014

(51) Int. Cl.
*G01N 27/49* (2006.01)
*G01N 27/327* (2006.01)
*G01N 33/487* (2006.01)

(52) U.S. Cl.
CPC .......... *G01N 27/49* (2013.01); *G01N 27/3273* (2013.01); *G01N 33/48707* (2013.01)

(58) Field of Classification Search
CPC ...... G01N 33/49; G01N 33/80; G01N 33/26; G01N 27/48; G01N 27/26; G01N 27/327; A61B 5/14535; A61B 5/05; A61B 5/14532
See application file for complete search history.

(56) References Cited

U.S. PATENT DOCUMENTS

| | | | |
|---|---|---|---|
| 4,919,770 A | 4/1990 | Preidel et al. | |
| 5,942,102 A | 8/1999 | Hodges et al. | |
| 6,413,410 B1 | 7/2002 | Hodges et al. | |
| 7,749,371 B2 | 7/2010 | Guo et al. | |
| 7,972,861 B2 | 7/2011 | Deng et al. | |
| 8,163,162 B2 | 4/2012 | Chatelier et al. | |
| 2009/0223834 A1 | 9/2009 | Cai et al. | |
| 2010/0206749 A1 | 8/2010 | Choi | |
| 2013/0220836 A1* | 8/2013 | Kermani et al. | 205/782 |

OTHER PUBLICATIONS

U.S. Appl. No. 61/530,795, filed Sep. 2, 2011.
U.S. Appl. No. 61/530,808, filed Sep. 2, 2011.
Wegener, Joachim et al., "Electric Cell—Substrate Impedance Sensing (ECIS) as a Noninvasive Means to Monitor the Kinetics of Cell Spreading to Artificial Surfaces," Experimental Cell Research 259, 158-166 (2000) doi:10.1006/excr.2000.4919.
Kohma, Takuya et al., "Utilization of AC Impedance Measurements for Electrochemical Glucose Sensing Using Glucose Oxidase to Improve Detection Selectivity," Bull. Chem. Soc. Jpn. vol. 80, No. 1, 158-165 (2007).
Jopling, J. et al., "Reference Ranges for Hematocrit and Blood Hemoglobin Concentration During the Neonatal period: Data from a Multihospital Health Care System," Pediatrics, vol. 123, N. 2, Feb. 2009, pp. 333-337.

* cited by examiner

*Primary Examiner* — Gurpreet Kaur

(57) ABSTRACT

Described are methods and systems to apply a plurality of test voltages to the test strip and measure a current transient output resulting from an electrochemical reaction in a test chamber of the test strip so that a glucose concentration can be determined that account for hematocrits in both typical subjects and neonates.

8 Claims, 13 Drawing Sheets

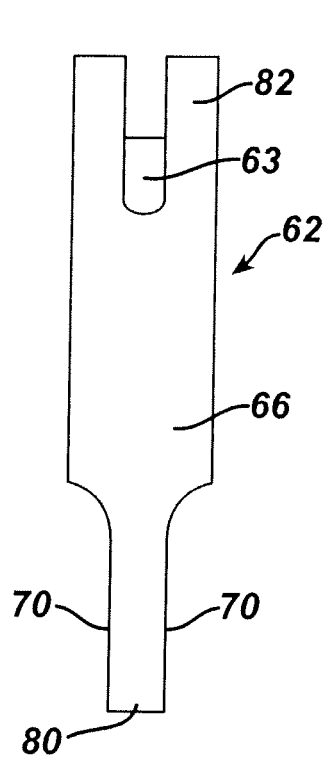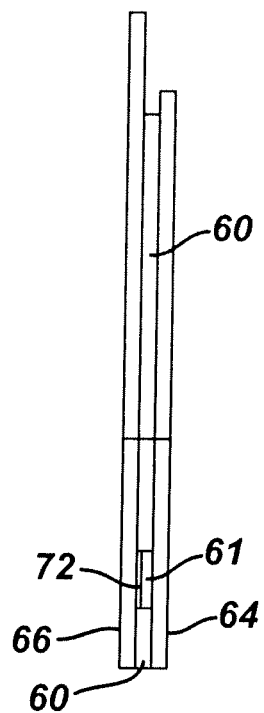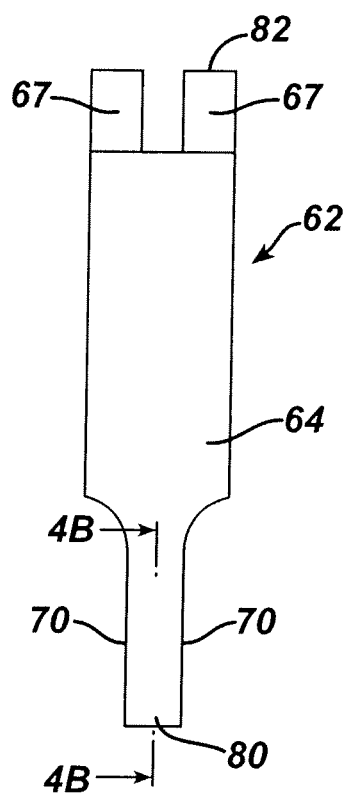
FIG. 2   FIG. 3   FIG. 4A
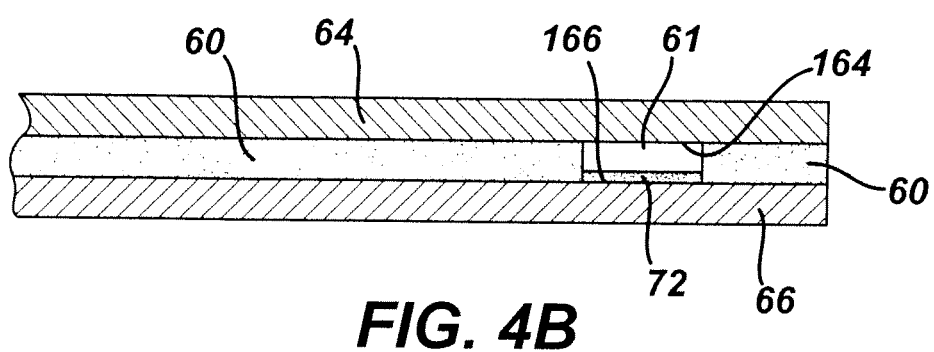
FIG. 4B

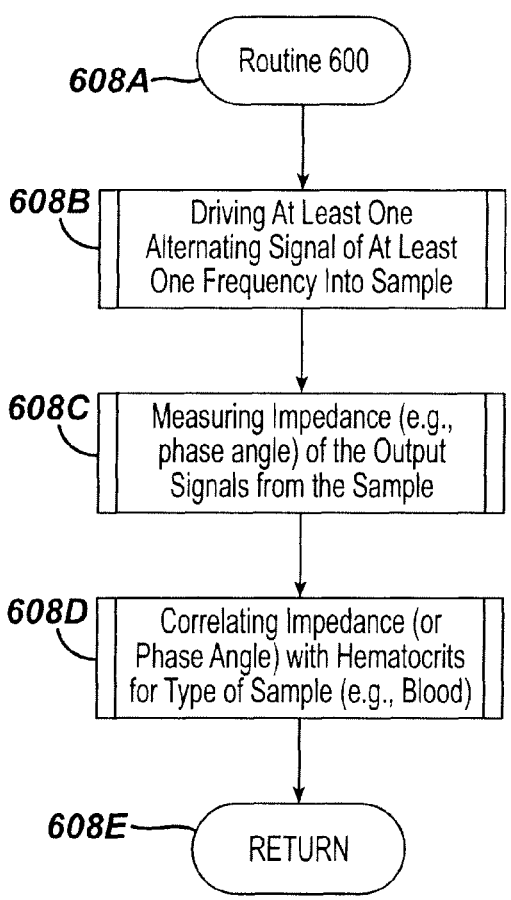
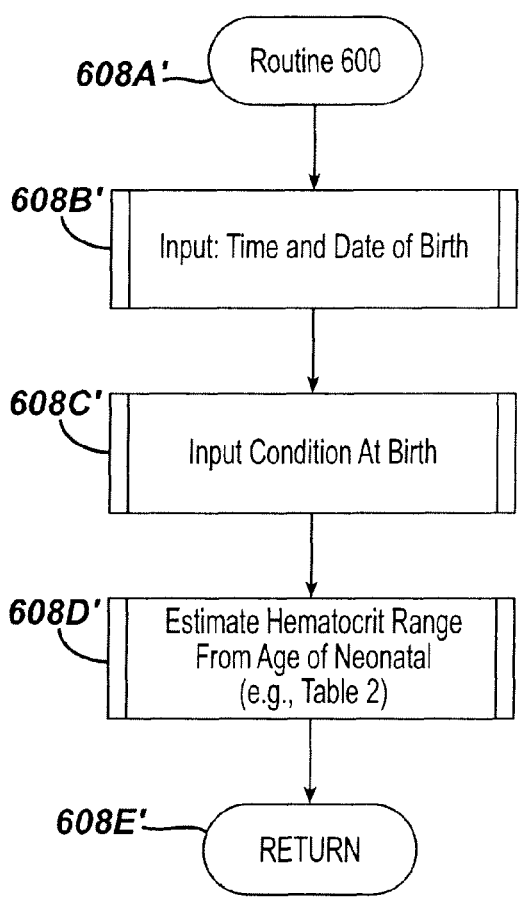
*FIG. 6B*                *FIG. 6C*

SYSTEM AND METHOD FOR MEASURING AN ANALYTE IN A SAMPLE AND CALCULATING GLUCOSE RESULTS TO ACCOUNT FOR PHYSICAL CHARACTERISTICS OF THE SAMPLE

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency or error. For example, hematocrits and interferents may affect the results of the method.

SUMMARY OF THE DISCLOSURE

Applicants have discovered a technique to allow for greater precision and accuracy in analyte measurements despite varying levels of substances that are present in the sample and which may affect the physical characteristic(s) of the sample. In one aspect, applicants have devised a method of determining blood glucose concentration with a glucose measurement system that includes a test strip and test meter. The test meter has a microcontroller configured to apply a plurality of test voltages to the test strip and measure a current transient output resulting from an electrochemical reaction in a test chamber of the test strip. The method can be achieved by: inserting the test strip into a strip port connector of the test meter to connect at least two electrodes of the test strip to a strip measurement circuit; initiating a test sequence after deposition of a sample; determining at least one physical characteristic of the sample; transforming analytes in the sample from one form to a different form; switching the first voltage to a second voltage different than the first voltage; changing the second voltage to a third voltage different from the second voltage; measuring a second current output of the current transient from the electrodes after the changing from the second voltage to the third voltage; estimating a current that approximates a steady state current output of the current transient after the third voltage is maintained at the electrodes; obtaining analyte calculation coefficients of the test chamber based on the at least one physical characteristic of the sample; and calculating a blood glucose concentration based on the first, second and third current outputs of the current transient and the analyte calculation coefficients from the obtaining step.

In yet another aspect, applicants have devised a method of determining blood glucose concentration with a glucose measurement system that includes a test strip and test meter. The test meter has a microcontroller configured to apply a plurality of test voltages to the test strip and measure a current transient output resulting from an electrochemical reaction in a test chamber of the test strip. The method can be achieved by: initiating a test sequence after deposition of a sample; transforming analytes in the sample from one form to a different form; switching the first voltage to a second voltage different than the first voltage; changing the second voltage to a third voltage different from the second voltage; measuring a second current output of the current transient from the electrodes after the changing from the second voltage to the third voltage; estimating approximate steady state current output of the current transient after the third voltage is maintained at the electrodes; calculating a blood glucose concentration based on the first, second and third current outputs of the current transient with an equation of the form:

$$G = \left(\frac{|i_r|}{|i_l|}\right)^p (a|i_{2CORR}| - zgr);$$

where: $G$ comprises a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right) i_r$$

where:
a may be about 0.171;
b may be about 0.678;
c may be about 2;
p may be about 0.433;
zgr may be about 4;
$i_{4.1}$ may be the current measured at about 4.1 seconds after initiation of test sequence;
$i_5$ may be the current measured at about 5 seconds after initiation of test sequence;
$i_{1.1}$ may be the current measured at about 1.1 seconds after initiation of test sequence.

In each of the above aspects, the following features may be combined separately with or together with each other and with the above noted aspects. For example, the step of switching may be changing the polarity of the second voltage with respect to the first voltage; the determining of the at least one physical characteristic of the sample comprises: Driving an alternating signal into the test chamber; measuring an impedance from an output signal of the test chamber; and correlating the impedance with a hematocrit level of the sample; the determining of the at least one physical characteristic of the sample comprises: determining an age of the subject from birth to no more than one year old; and Selecting a hematocrit level based on the age; the obtaining may be selecting from a look-up table having the analyte calculation coefficients for each level of hematocrit; or the glucose calculation is obtained with an equation of the form:

$$G = \left(\frac{|i_r|}{|i_l|}\right)^p (a|i_{2CORR}| - zgr);$$

where: $G$ may be a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right) i_r$$

where:
a, p, and zgr are determined from the obtaining step;
b may be about 0.205;
c may be about 2;
$i_{4.1}$ may be the current measured at about 4.1 seconds after initiation of test sequence;
$i_5$ may be the current measured at about 5 seconds after initiation of test sequence;
$i_{1.1}$ may be the current measured at about 1.1 seconds after initiation of test sequence.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 2 is a bottom plan view of one embodiment of a test strip disclosed herein;

FIG. 3 is a side plan view of the test strip of FIG. 2;

FIG. 4A is a top plan view of the test strip of FIG. 3;

FIG. 4B is a partial side view of a proximal portion of the test strip of FIG. 4A;

FIG. 6B illustrates the details of step 608 to directly determine the physical characteristic of the sample in the logic 600 of FIG. 6A;

FIG. 6C illustrates the details of an alternate technique to obtain the hematocrit range of neonatal subjects for the logic 600 of FIG. 6A;

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1A:
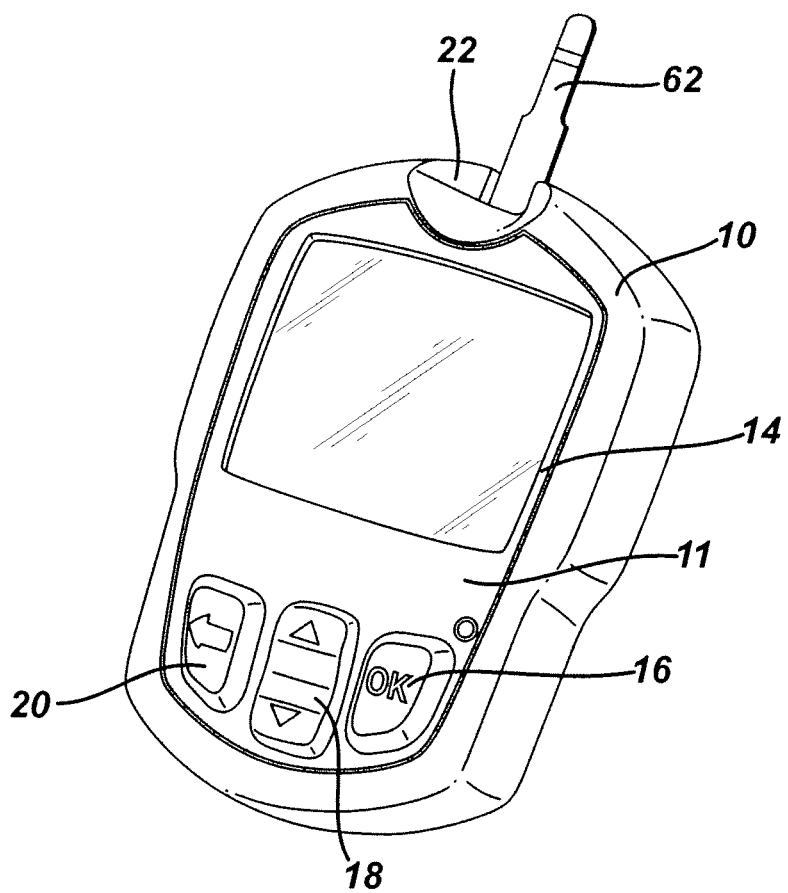
FIG. 1A illustrates a preferred blood glucose measurement system.

FIG. 1A illustrates a diabetes management system that includes a meter 10 and a biosensor in the form of a glucose test strip 62. Note that the meter (meter unit) may be referred to as an analyte measurement and management unit, a glucose meter, a meter, and an analyte measurement device. In an embodiment, the meter unit may be combined with an insulin delivery device, an additional analyte testing device, and a drug delivery device. The meter unit may be connected to a remote computer or remote server via a cable or a suitable wireless technology such as, for example, GSM, CDMA, BlueTooth, WiFi and the like.

Referring back to FIG. 1A, glucose meter or meter unit 10 may include a housing 11, user interface buttons (16, 18, and 20), a display 14, and a strip port opening 22. User interface buttons (16, 18, and 20) may be configured to allow the entry of data, navigation of menus, and execution of commands. User interface button 18 may be in the form of a two way toggle switch. Data may include values representative of analyte concentration, or information, which are related to the everyday lifestyle of an individual. Information, which is related to the everyday lifestyle, may include food intake, medication use, occurrence of health check-ups, and general health condition and exercise levels of an individual. The electronic components of meter 10 may be disposed on a circuit board 34 that is within housing 11.

Figure 1B:
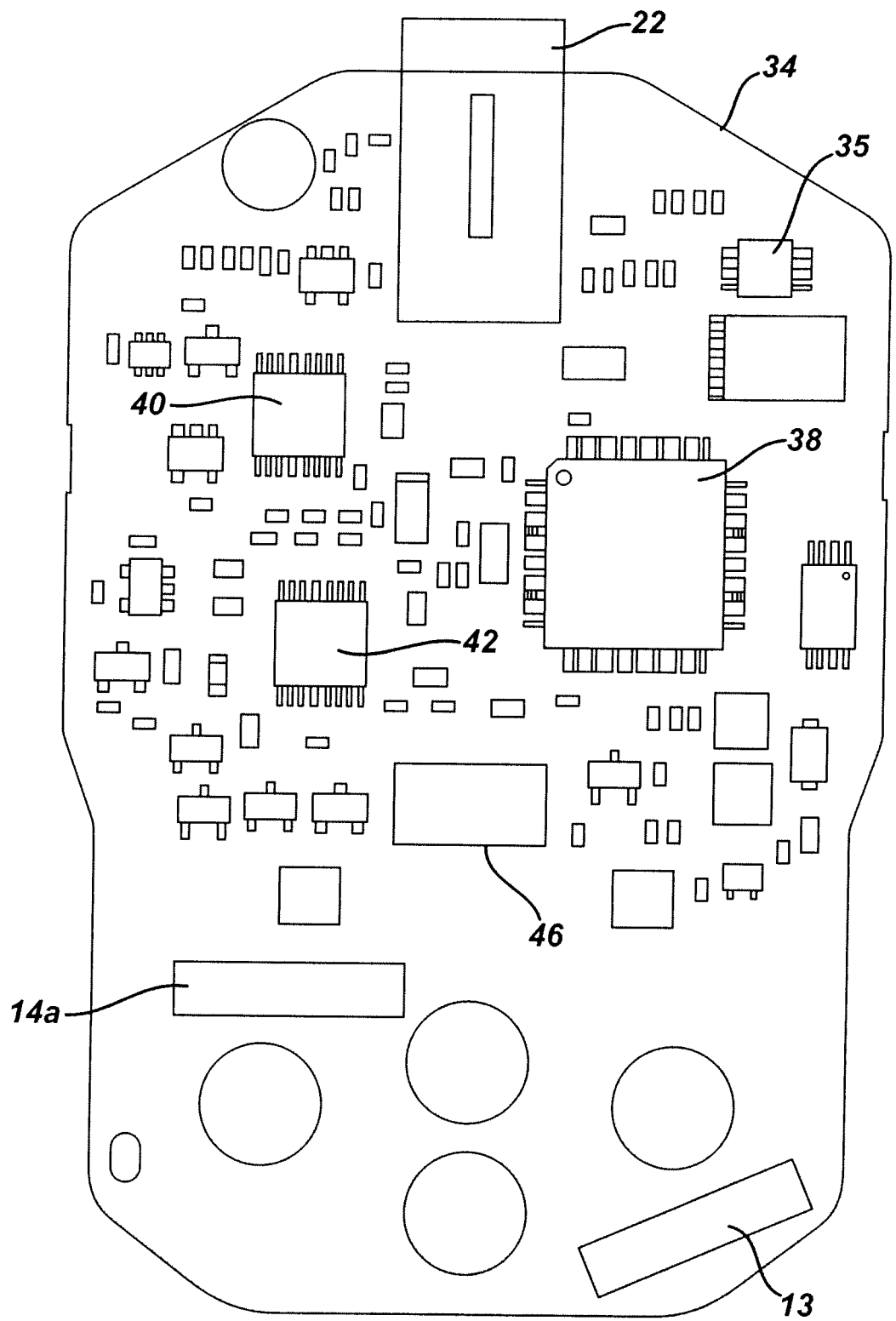
FIG. 1B illustrates the various components disposed in the meter of FIG. 1A.

FIG. 1B illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock 42, and a first wireless module 46. On the bottom surface, the electronic components may include a battery connector (not shown) and a data port 13. Microcontroller 38 may be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 may include two or more operational amplifiers configured to provide a portion of the potentiostat function and the current measurement function. The potentiostat function may refer to the application of a test voltage between at least two electrodes of a test strip. The current function may refer to the measurement of a test current resulting from the applied test voltage. The current measurement may be performed with a current-to-voltage converter. Microcontroller 38 may be in the form of a mixed signal microprocessor (MSP) such as, for example, the Texas Instrument MSP 430. The TI-MSP 430 may be configured to also perform a portion of the potentiostat function and the current measurement function. In addition, the MSP 430 may also include volatile and non-volatile memory. In another embodiment, many of the electronic components may be integrated with the microcontroller in the form of an application specific integrated circuit (ASIC).

Strip port connector 22 may be configured to form an electrical connection to the test strip. Display connector 14a may be configured to attach to display 14. Display 14 may be in the form of a liquid crystal display for reporting measured glucose levels, and for facilitating entry of lifestyle related information. Display 14 may optionally include a backlight. Data port 13 may accept a suitable connector attached to a connecting lead, thereby allowing glucose meter 10 to be linked to an external device such as a personal computer. Data port 13 may be any port that allows for transmission of data such as, for example, a serial, USB, or a parallel port. Clock 42 may be configured to keep current time related to the geographic region in which the user is located and also for measuring time. The meter unit may be configured to be electrically connected to a power supply such as, for example, a battery.

Figure 1C:
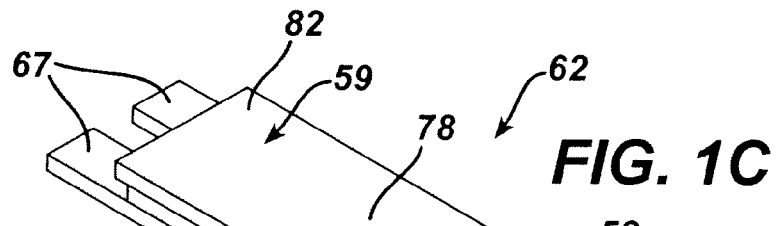
FIG. 1C illustrates a perspective view of an assembled test strip suitable for use in the system and methods disclosed herein.
Figure 1D:
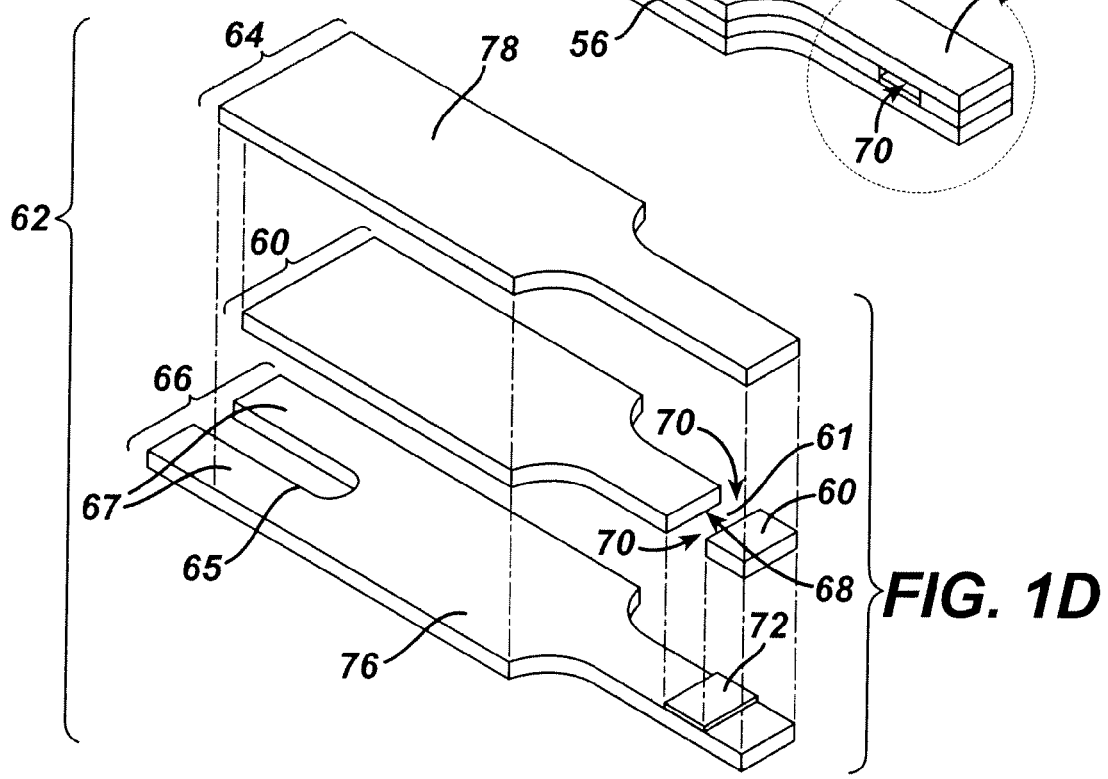
FIG. 1D illustrates an exploded perspective view of an unassembled test strip suitable for use in the system and methods disclosed herein.

FIGS. 1C-1E, 2, 3, and 4B show various views of an exemplary test strip 62 suitable for use with the methods and systems described herein. In an exemplary embodiment, a test strip 62 is provided which includes an elongate body extending from a distal end 80 to a proximal end 82, and having lateral edges 56, 58, as illustrated in FIG. 1C. As shown in FIG. 1D, the test strip 62 also includes a first electrode layer 66, a second electrode layer 64, and a spacer 60 sandwiched in between the two electrode layers 64 and 66. The first electrode layer 66 may include a first electrode 66, a first connection track 76, and a first contact pad 67, where the first connection track 76 electrically connects the first electrode 66 to the first contact pad 67, as shown in FIGS. 1D and 4B. Note that the first electrode 66 is a portion of the first electrode layer 66 that is immediately underneath the reagent layer 72, as indicated by FIGS. 1D and 4B. Similarly, the second electrode layer 64 may include a second electrode 64, a second connection track 78, and a second contact pad 63, where the second connection track 78 electrically connects the second electrode 64 with the second contact pad 63, as shown in FIGS. 1D, 2, and 4B. Note that the second electrode 64 is a portion of the second electrode layer 64 that is above the reagent layer 72, as indicated by FIG. 4B.

Figure 1E:
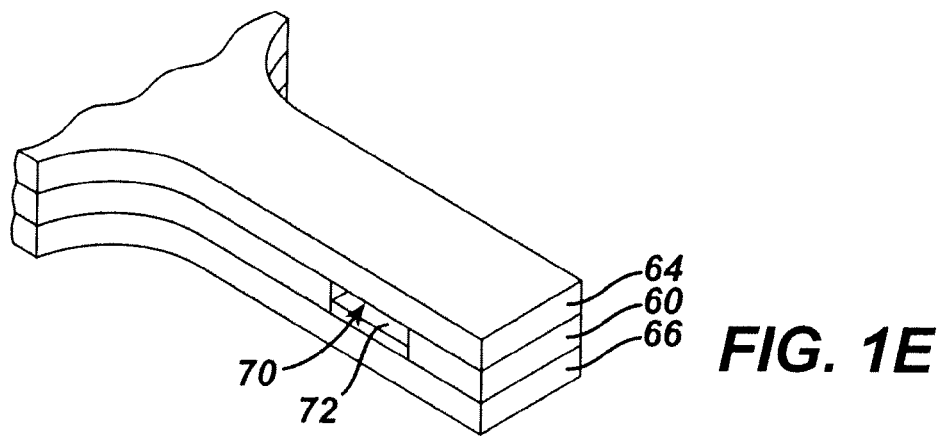
FIG. 1E illustrates an expanded perspective view of a proximal portion of the test strip suitable for use in the system and methods disclosed herein.

As shown, the sample-receiving chamber 61 is defined by the first electrode 66, the second electrode 64, and the spacer 60 near the distal end 80 of the test strip 62, as shown in FIGS. 1D and 4B. The first electrode 66 and the second electrode 64 may define the bottom and the top of sample-receiving chamber 61, respectively, as illustrated in FIG. 4B. A cutout area 68 of the spacer 60 may define the sidewalls of the sample-receiving chamber 61, as illustrated in FIG. 4B. In one aspect, the sample-receiving chamber 61 may include ports 70 that provide a sample inlet or a vent, as shown in FIGS. 1C to 1E. For example, one of the ports may allow a fluid sample to ingress and the other port may allow air to egress.

In an exemplary embodiment, the sample-receiving chamber 61 (or test cell or test chamber) may have a small volume. For example, the chamber 61 may have a volume in the range of from about 0.1 microliters to about 5 microliters, about 0.2 microliters to about 3 microliters, or, preferably, about 0.3 microliters to about 1 microliter. To provide the small sample volume, the cutout 68 may have an area ranging from about 0.01 $cm^2$ to about 0.2 $cm^2$, about 0.02 $cm^2$ to about 0.15 $cm^2$, or, preferably, about 0.03 $cm^2$ to about 0.08 $cm^2$. In addition, first electrode 66 and second electrode 64 may be spaced apart in the range of about 1 micron to about 500 microns, preferably between about 10 microns and about 400 microns, and more preferably between about 40 microns and about 200 microns. The relatively close spacing of the electrodes may also allow redox cycling to occur, where oxidized mediator generated at first electrode 66, may diffuse to second electrode 64 to become reduced, and subsequently diffuse back to first electrode 66 to become oxidized again. Those skilled in the art will appreciate that various such volumes, areas, or spacing of electrodes is within the spirit and scope of the present disclosure.

In one embodiment, the first electrode layer 66 and the second electrode layer 64 may be a conductive material formed from materials such as gold, palladium, carbon, silver, platinum, tin oxide, iridium, indium, or combinations thereof (e.g., indium doped tin oxide). In addition, the electrodes may be formed by disposing a conductive material onto an insulating sheet (not shown) by a sputtering, electroless plating, or a screen-printing process. In one exemplary embodiment, the first electrode layer 66 and the second electrode layer 64 may be made from sputtered palladium and sputtered gold, respectively. Suitable materials that may be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated. Applicants note that various other materials for the first electrode layer 66, the second electrode layer 64, or the spacer 60 are within the spirit and scope of the present disclosure.

Either the first electrode 66 or the second electrode 64 may perform the function of a working electrode depending on the magnitude or polarity of the applied test voltage. The working electrode may measure a limiting test current that is proportional to the reduced mediator concentration. For example, if the current limiting species is a reduced mediator (e.g., ferrocyanide), then it may be oxidized at the first electrode 66 as long as the test voltage is sufficiently greater than the redox mediator potential with respect to the second electrode 64. In such a situation, the first electrode 66 performs the function of the working electrode and the second electrode 64 performs the function of a counter/reference electrode. Applicants note that one may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term "bulk solution" refers to a portion of the solution sufficiently far away from the working electrode where the reduced mediator is not located within a depletion zone. It should be noted that unless otherwise stated for test strip 62, all potentials applied by test meter 10 will hereinafter be stated with respect to second electrode 64.

Similarly, if the test voltage is sufficiently less than the redox mediator potential, then the reduced mediator may be oxidized at the second electrode 64 as a limiting current. In such a situation, the second electrode 64 performs the function of the working electrode and the first electrode 66 performs the function of the counter/reference electrode.

Initially, an analysis may include introducing a quantity of a fluid sample into a sample-receiving chamber 61 via a port 70. In one aspect, the port 70 or the sample-receiving chamber 61 may be configured such that capillary action causes the fluid sample to fill the sample-receiving chamber 61. The first electrode 66 or second electrode 64 may be coated with a hydrophilic reagent to promote the capillarity of the sample-receiving chamber 61. For example, thiol derivatized reagents having a hydrophilic moiety such as 2-mercaptoethane sulfonic acid may be coated onto the first electrode or the second electrode.

In the analysis of strip 62 above, reagent layer 72 can include glucose dehydrogenase (GDH) based on the PQQ co-factor and ferricyanide. In another embodiment, the enzyme GDH based on the PQQ co-factor may be replaced with the enzyme GDH based on the FAD co-factor. When blood or control solution is dosed into a sample reaction chamber 61, glucose is oxidized by $GDH_{(ox)}$ and in the process converts $GDH_{(ox)}$ to $GDH_{(red)}$, shown in the chemical transformation T.1 below. Note that $GDH_{(ox)}$ refers to the oxidized state of GDH, and $GDH_{(red)}$ refers to the reduced state of GDH.

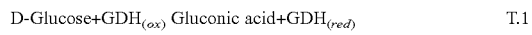

D-Glucose+$GDH_{(ox)}$ Gluconic acid+$GDH_{(red)}$  T.1

Next, $GDH_{(red)}$ is regenerated back to its active oxidized state by ferricyanide (i.e. oxidized mediator or $Fe(CN)_6^{3-}$) as shown in chemical transformation T.2 below. In the process of regenerating $GDH_{(ox)}$, ferrocyanide (i.e. reduced mediator or $Fe(CN)_6^{4-}$) is generated from the reaction as shown in T.2:

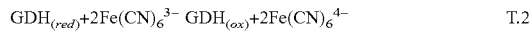

$GDH_{(red)}$+2$Fe(CN)_6^{3-}$ $GDH_{(ox)}$+2$Fe(CN)_6^{4-}$  T.2

Figure 5:
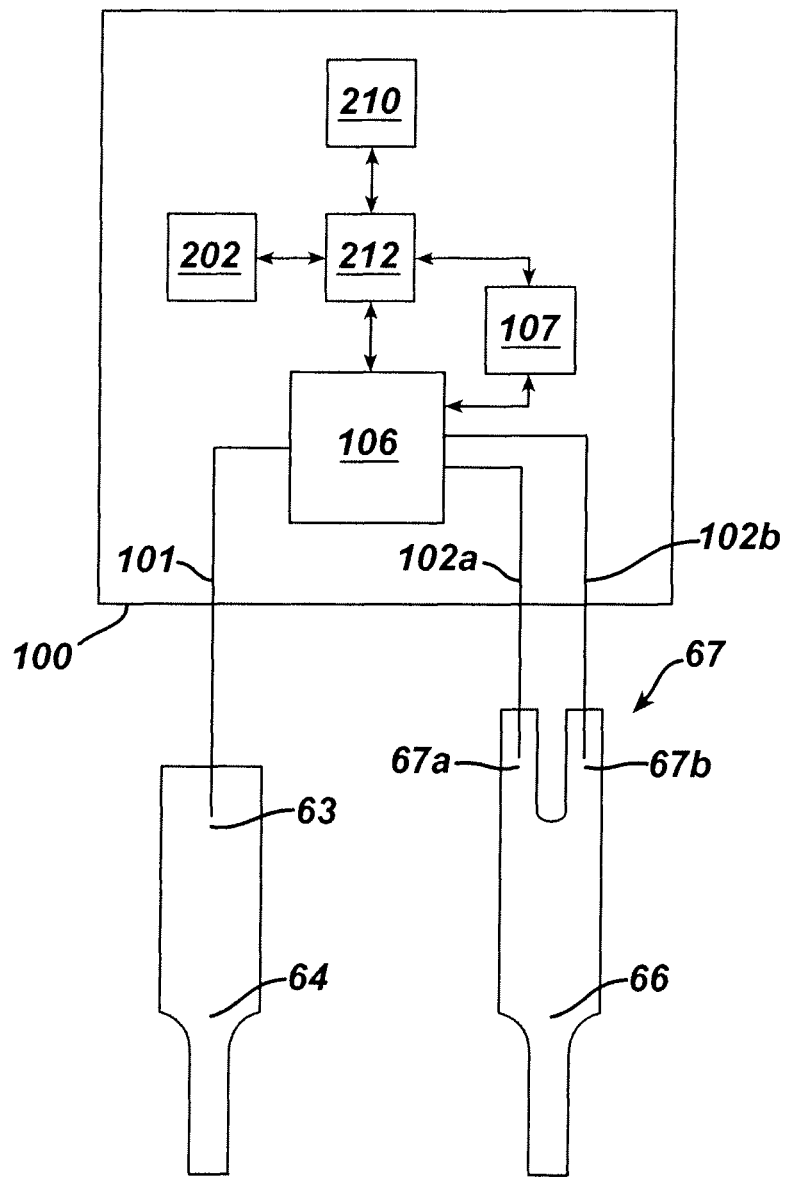
FIG. 5 is a simplified schematic showing a test meter electrically interfacing with portions of a test strip disclosed herein.

FIG. 5 provides a simplified schematic showing a test meter 100 interfacing with a first contact pad 67a, 67b and a second contact pad 63. The second contact pad 63 may be used to establish an electrical connection to the test meter through a U-shaped notch 65, as illustrated in FIG. 2. In one embodiment, the test meter 100 may include a second electrode connector 101, and a first electrode connectors (102a, 102b), a test voltage unit 106, a current measurement unit 107, a processor 212, a memory unit 210, and a visual display 202, as shown in FIG. 5. The first contact pad 67 may include two prongs denoted as 67a and 67b. In one exemplary embodiment, the first electrode connectors 102a and 102b separately connect to prongs 67a and 67b, respectively. The second electrode connector 101 may connect to second contact pad 63. The test meter 100 may measure the resistance or electrical continuity between the prongs 67a and 67b to determine whether the test strip 62 is electrically connected to the test meter 10. The electrodes 64 and 66 here can be utilized to detect physical characteristics of the sample using alternating signals. Alternatively, separate additional electrodes can be provided in the test chamber to allow for detection of the physical characteristics of the sample using alternating signals.

Figure 6A:
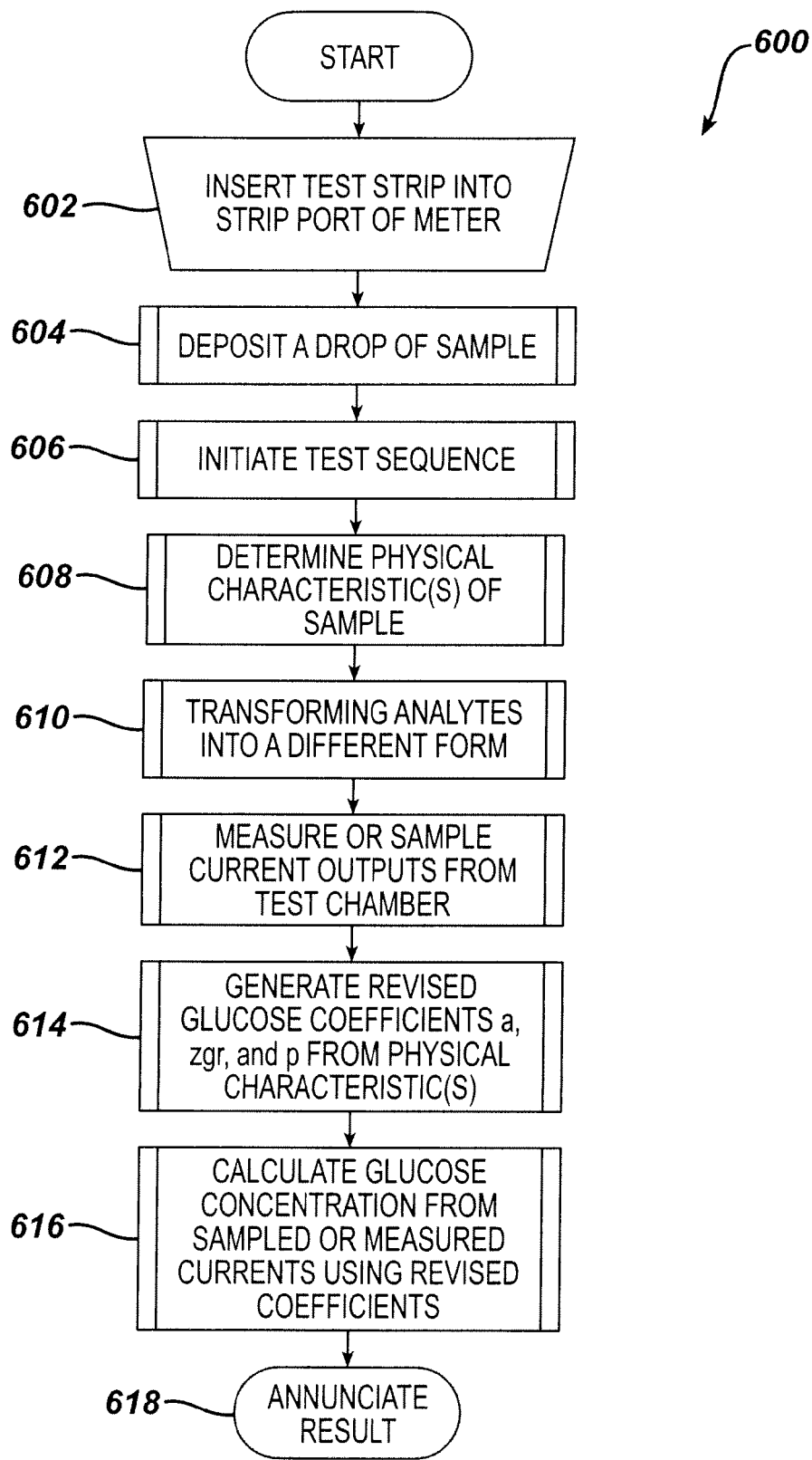
FIG. 6A illustrates a flowchart 600 of the applicants' technique to determine an accurate glucose concentration.

Referring to FIG. 6A, a method 600 for determining an interferent-corrected analyte concentration (e.g., glucose concentration) that uses the aforementioned meter 10 and test strip 62 embodiments will now be described.

In exemplary method 600, meter 10 and biosensor 62 are provided as part of the method. Meter 10 may include electronic circuitry that can be used to apply a plurality of voltages to the test strip 62 and to measure a current transient output resulting from an electrochemical reaction in a test chamber of the test strip 62. Meter 10 also may include a signal processor with a set of instructions for the method of determining an analyte concentration in a fluid sample as disclosed herein.

The method can be achieved starting with step 602 with the user inserting the test strip into a strip port connector of the test meter to connect at least two electrodes of the test strip to a strip measurement circuit. In this method, the test meter 100 may apply a test voltage or a current between the first contact pad 67 and the second contact pad 63. Once the test meter 100 recognizes that the strip 62 has been inserted from step 602, the test meter 100 turns on and initiates a fluid detection mode. In the exemplary method, the fluid detection mode causes test meter 100 to apply a constant current of about 1 microampere between the first electrode 66 and the second electrode 64. Because the test strip 62 is initially dry, the test meter 10 measures a relatively large voltage. When the fluid sample is deposited onto the test chamber in step 604, the sample bridges the gap between the first electrode 66 and the second electrode 64 and the test meter 100 will measure a decrease in measured voltage that is below a predetermined threshold causing test meter 10 to automatically initiate the glucose test in step 606 by application of a first voltage potential E1. At step 608, the system determines at least one physical characteristic of the sample, such as, for example, viscosity, temperature, or preferably hematocrits.

Step 608 may include two techniques of deriving the hematocrits of the sample. In the first technique, shown here in FIG. 6B, the hematocrit level is obtained by directly sensing the sample using alternating signals injected to the sample at a certain frequency (or frequencies). In the second alternative, the hematocrit range can be determined through a technique devised by applicants, which will be discussed later in this disclosure. With regard to the first technique in FIG. 6A at step 608, which is further illustrated in FIG. 6B, step 608A indicates that the prior steps can be any step in logic 600 as long as the prior step is not the output of the glucose result. At step 608B in FIG. 6B, the system may apply a first oscillating input signal at a first frequency (e.g., of about 25 kilo-Hertz) to the pair of electrodes or separate hematocrit sensing electrodes. The system is also set up to measure or detect a first oscillating output signal from these electrodes, which in particular involve measuring a first time differential $\Delta t_1$ between the first input and output oscillating signals. At the same time or during overlapping time durations, the system may also apply a second oscillating input signal (not shown for brevity) at a second frequency (e.g., about 100 kilo-Hertz to about 1 MegaHertz or higher, and preferably about 250 kilo Hertz) to the pair of electrodes and then measure or detect a second oscillating output signal from the third and fourth electrodes, which may involve measuring a second time differential $\Delta t_2$ (not shown) between the first input and output oscillating signals. From these signals, the system estimate a physical characteristic (e.g., hematocrit) of the blood sample based on the first and second time differentials $\Delta t_1$ and $\Delta t_2$. Thereafter, the system is able to derive a glucose concentration. The estimate of the physical characteristic (e.g., hematocrit) can be done by applying an equation of the form $$HCT_{EST} = \frac{(C_1 \Delta t_1 - C_2 \Delta t_2 - C_3)}{m_1}. \qquad \text{Equation A}$$

Where each of $C_1$, $C_2$, and $C_3$ is an operational constant for the test strip.

At step 608D, the hematocrit is correlated using Equation A. Details of this exemplary technique can be found in Provisional U.S. patent application Ser. No. 61/530,795 filed on Sep. 2, 2011, entitled, "Hematocrit Corrected Glucose Measurements for Electrochemical Test Strip Using Time Differential of the Signals", which is hereby incorporated by reference with a copy provided in the Appendix.

Although one technique has been described, there are other techniques available to one skilled in the art to determine the physical characteristics of the sample. For example, the physical characteristic (e.g., hematocrit) can be determined by two independent measurements. This can be obtained by determining: (a) the impedance of the blood sample at a first frequency and (b) the phase angle of the blood sample at a second frequency substantially higher than the first frequency. In this technique, the blood sample is modeled as a circuit having unknown reactance and unknown resistance. With this model, an impedance (as signified by notation "|Z|") for measurement (a) can be determined from the applied voltage, the voltage across a known resistor (e.g., the intrinsic strip resistance), and the voltage across the unknown impedance Vz; and similarly, for measurement (b) the phase angle can be measured from a time difference between the input and output signals by those skilled in the art. Details of this technique are shown and described in pending provisional patent application Ser. No. 61/530,808 filed Sep. 2, 2011, which is incorporated by reference with a copy attached to the Appendix. Other suitable techniques for determining the physical characteristic (e.g., hematocrit, viscosity, or density) of the physiological fluid sample can also be utilized such as, for example, U.S. Pat. Nos. 4,919,770, 7,972,861, US Patent Application Publication Nos. 2010/0206749, 2009/0223834, or "Electric Cell-Substrate Impedance Sensing (ECIS) as a Noninvasive Means to Monitor the Kinetics of Cell Spreading to Artificial Surfaces" by Joachim Wegener, Charles R. Keese, and Ivar Giaever and published by Experimental Cell Research 259, 158-166 (2000) doi:10.1006/excr.2000.4919, available online at http://www.idealibrary.coml; "Utilization of AC Impedance Measurements for Electrochemical Glucose Sensing Using Glucose Oxidase to Improve Detection Selectivity" by Takuya Kohma, Hidefumi Hasegawa, Daisuke Oyamatsu, and Susumu Kuwabata and published by Bull. Chem. Soc. Jpn. Vol. 80, No. 1, 158-165 (2007), all of these documents are incorporated by reference with a copy attached hereto the Appendix.

Returning back to FIG. 6B, once the hematocrit has been determined in step 608D, the logic returns via step 608E to the main routine 600 of FIG. 6A.

At step 610 in process 600 of FIG. 6A, the analyte in the sample is transformed from one form (e.g., glucose) into a different form (e.g., gluconic acid) due to an electrochemical reaction in the test chamber. As part of step 610, the system proceeds by switching the first voltage potential from E1 to a second voltage potential E2 different than the first voltage (FIG. 7A), then the system further proceeds by changing the second voltage to a third voltage E3 different from the second voltage E2 (FIG. 7A).

Figure 7A:
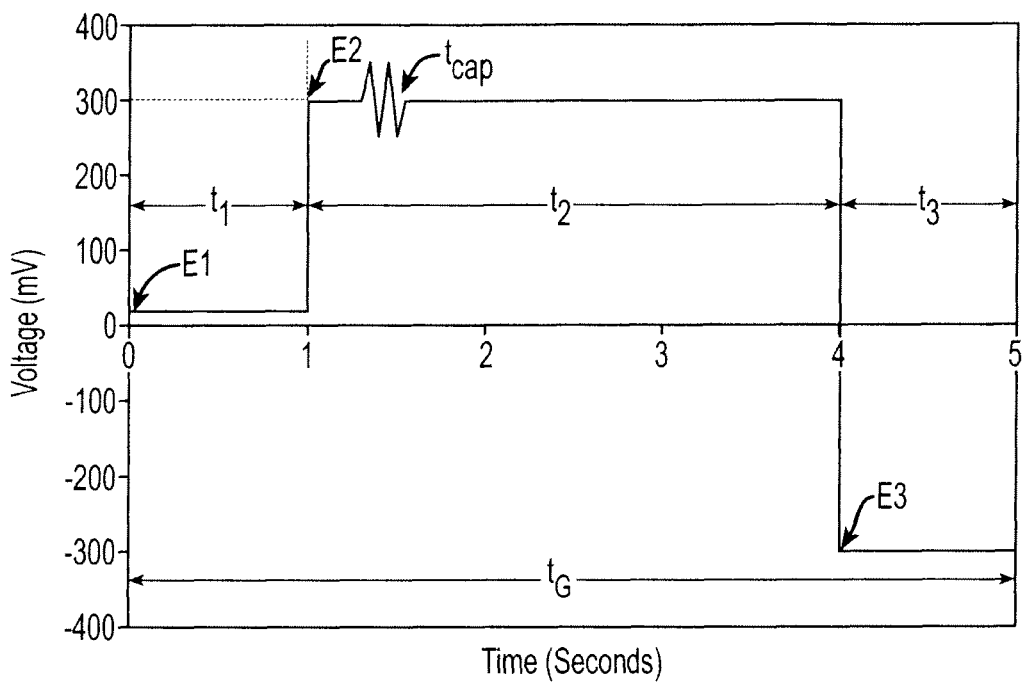
FIG. 7A shows an example of a tri-pulse potential waveform applied by the test meter of FIG. 5 to the working and counter electrodes for prescribed time intervals.

FIG. 7A is an exemplary chart of a plurality of test voltages applied to the test strip 62 for prescribed intervals. The plurality of test voltages may include a first test voltage E1 for a first time interval $t_1$, a second test voltage E2 for a second time interval $t_2$, and a third test voltage E3 for a third time interval $t_3$. The third voltage E3 may be different in the magnitude of the electromotive force, in polarity, or combinations of both with respect to the second test voltage E2. In the preferred embodiments, E3 may be of the same magnitude as E2 but opposite in polarity. A glucose test time interval $t_G$ represents an amount of time to perform the glucose test (but not necessarily all the calculations associated with the glucose test). Glucose test time interval $t_G$ may range from about 1.1 seconds to about 5 seconds. Further, as illustrated in FIG. 7A, the second test voltage E2 may include a direct (DC) test voltage component and a superimposed alternating (AC), or alternatively oscillating, test voltage component. The superimposed alternating or oscillating test voltage component may be applied for a time interval indicated by $t_{cap}$.

The plurality of test current values measured during any of the time intervals may be performed at a sampling frequency ranging from about 1 measurement per microsecond to about one measurement per 100 milliseconds and preferably at about every 50 milliseconds. While an embodiment using three test voltages in a serial manner is described, the glucose test may include different numbers of open-circuit and test voltages. For example, as an alternative embodiment, the glucose test could include an open-circuit for a first time interval, a second test voltage for a second time interval, and a third test voltage for a third time interval. It should be noted that the reference to "first," "second," and "third" are chosen for convenience and do not necessarily reflect the order in which the test voltages are applied. For instance, an embodiment may have a potential waveform where the third test voltage may be applied before the application of the first and second test voltage.

In this exemplary system, the process for the system may apply a first test voltage E1 (e.g., approximately 20 mV in FIG. 7A) between first electrode 66 and second electrode 64 for a first time interval $t_1$ (e.g., 1 second in FIG. 7A). The first time interval $t_1$ may range from about 0.1 seconds to about 3 seconds and preferably range from about 0.2 seconds to about 2 seconds, and most preferably range from about 0.3 seconds to about 1.1 seconds.

Figure 7B:
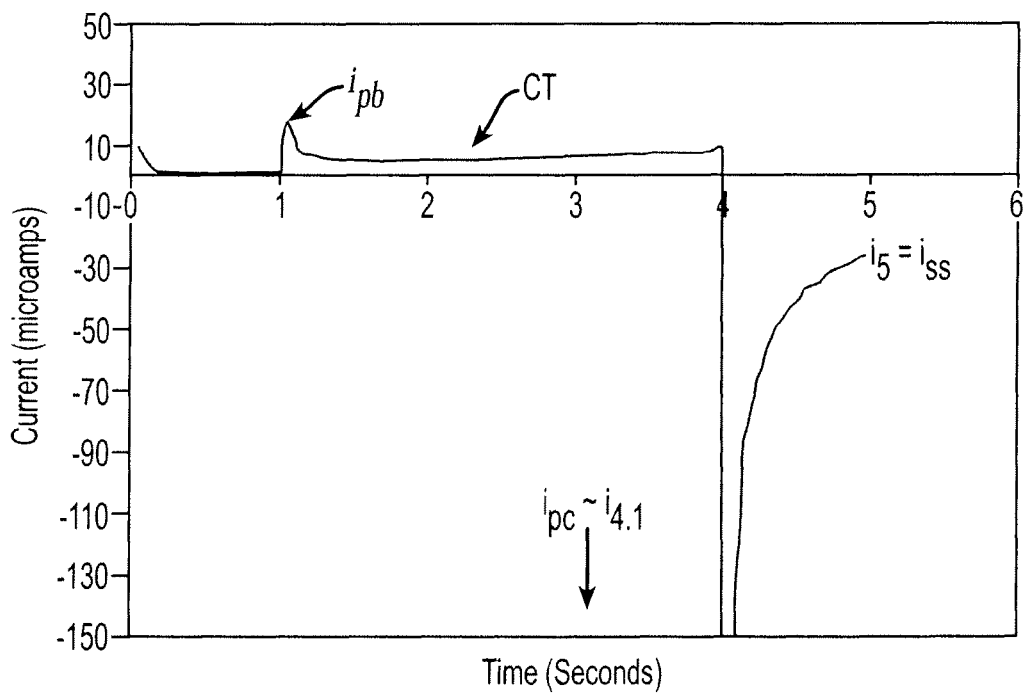
FIG. 7B shows a current transient CT generated by a physiological sample.

The first time interval $t_1$ may be sufficiently long so that the sample-receiving or test chamber 61 (defined partly by first wall 164 and second wall 166) may fully fill with sample and also so that the reagent layer 72 may at least partially dissolve or solvate. In one aspect, the first test voltage E1 may be a value relatively close to the redox potential of the mediator so that a relatively small amount of a reduction or oxidation current is measured. FIG. 7B shows that a relatively small amount of current is observed during the first time interval $t_1$ compared to the second and third time intervals $t_2$ and $t_3$. For example, when using ferricyanide or ferrocyanide as the mediator, the first test voltage E1 in FIG. 7A may range from about 1 millivolts ("mV") to about 100 mV, preferably range from about 5 mV to about 50 mV, and most preferably range from about 10 mV to about 30 mV. Although the applied voltages are given as positive values in the preferred embodiments, the same voltages in the negative domain could also be utilized to accomplish the intended purpose of the claimed invention.

Referring back to FIG. 7A, after applying the first test voltage E1, the test meter 10 applies a second test voltage E2 between first electrode 66 and second electrode 64 (e.g., approximately 300 mVolts in FIG. 7A), for a second time interval $t_2$ (e.g., about 3 seconds in FIG. 7A). The second test voltage E2 may be a value different than the first test voltage E1 and may be sufficiently negative of the mediator redox potential so that a limiting oxidation current is measured at the second electrode 64. For example, when using ferricyanide or ferrocyanide as the mediator, the second test voltage E2 may range from about zero mV to about 600 mV, preferably range from about 100 mV to about 600 mV, and more preferably is about 300 mV.

The second time interval $t_2$ should be sufficiently long so that the rate of generation of reduced mediator (e.g., ferrocyanide) may be monitored based on the magnitude of a limiting oxidation current. Reduced mediator is generated by enzymatic reactions with the reagent layer 72. During the second time interval $t_2$, a limiting amount of reduced mediator is oxidized at second electrode 64 and a non-limiting amount of oxidized mediator is reduced at first electrode 66 to form a concentration gradient between first electrode 66 and second electrode 64.

In an exemplary embodiment, the second time interval $t_2$ should also be sufficiently long so that a sufficient amount of ferricyanide may be diffused to the second electrode 64 or diffused from the reagent on the first electrode. A sufficient amount of ferricyanide is required at the second electrode 64 so that a limiting current may be measured for oxidizing ferrocyanide at the first electrode 66 during the third test voltage E3. The second time interval $t_2$ may be less than about 60 seconds, and preferably may range from about 1.1 seconds to about 10 seconds, and more preferably range from about 2 seconds to about 5 seconds. Likewise, the time interval indicated as $t_{cap}$ in FIG. 7A may also last over a range of times, but in one exemplary embodiment it has a duration of about 20 milliseconds. In one exemplary embodiment, the superimposed alternating test voltage component is applied after about 0.3 seconds to about 0.4 seconds after the application of the second test voltage E2, and induces a sine wave having a frequency of about 109 Hz with an amplitude of about +/−50 mV.

FIG. 7B shows a relatively small peak $i_{pb}$ after the beginning of the second time interval $t_2$ followed by a gradual increase of an absolute value of an oxidation current during the second time interval $t_2$. The small peak $i_{pb}$ occurs due oxidation of endogenous or exogenous reducing agents (e.g., uric acid) after a transition from first voltage E1 to second voltage E2. Thereafter, there is a gradual absolute decrease in oxidation current after the small peak $i_{pb}$ is caused by the generation of ferrocyanide by reagent layer 72, which then diffuses to second electrode 64.

As part of step 610, after application of the second test voltage E2, the test meter 10 applies a third test voltage E3 between the first electrode 66 and the second electrode 64 (e.g., about −300 mVolts in FIG. 7A) for a third time interval $t_3$ (e.g., 1 second in FIG. 7A). The third test voltage E3 may be a value sufficiently positive of the mediator redox potential so that a limiting oxidation current is measured at the first electrode 66. For example, when using ferricyanide or ferrocyanide as the mediator, the third test voltage E3 may range from about zero mV to about −600 mV, preferably range from about −100 mV to about −600 mV, and more preferably is about −300 mV.

The third time interval $t_3$ may be sufficiently long to monitor the diffusion of reduced mediator (e.g., ferrocyanide) near the first electrode 66 based on the magnitude of the oxidation current. During the third time interval $t_3$, a limiting amount of reduced mediator is oxidized at first electrode 66 and a non-limiting amount of oxidized mediator is reduced at the second electrode 64. The third time interval $t_3$ may range from about 0.1 seconds to about 5 seconds and preferably range from about 0.3 seconds to about 3 seconds, and more preferably range from about 0.5 seconds to about 2 seconds.

FIG. 7B shows a relatively large peak $i_{pc}$ at the beginning of the third time interval $t_3$ followed by a decrease to a steady-state current $i_{ss}$ value. In one embodiment, the second test voltage E2 may have a first polarity and the third test voltage E3 may have a second polarity that is opposite to the first polarity. In another embodiment, the second test voltage E2 may be sufficiently negative of the mediator redox potential and the third test voltage E3 may be sufficiently positive of the mediator redox potential. The third test voltage E3 may be applied immediately after the second test voltage E2. However, one skilled in the art will appreciate that the magnitude and polarity of the second and third test voltages may be chosen depending on the manner in which analyte concentration is determined.

Referring to FIG. 7B, the system at step 612 also measure a second current output of the current transient from the electrodes after the changing from the second voltage to the third voltage and then the system proceeds by estimating a current that approximates a steady state current output of the current transient after the third voltage is maintained at the electrodes.

To ensure that the analyte measured is unaffected by hematocrit, the system, at step 614 obtains analyte calculation coefficients of the test chamber based on the at least one physical characteristic of the sample obtained from step 608, which in the preferred embodiments is hematocrits. Thereafter, at step 616, the system calculates a blood glucose concentration based on the first, second and third current outputs of the current transient and the analyte calculation coefficients from the obtaining step.

The glucose concentration G may be calculated using a glucose algorithm as shown in Equation 1:

$$G = \left(\frac{|i_2|}{|i_3|}\right)^p (a \times i_1 - z) \qquad \text{Eq. 1}$$

Where
$i_1$ is a first test current value,
$i_2$ is a second test current value,
$i_3$ is a third test current value, and
the terms a, p, and z can be empirically derived analyte calculation coefficients.

All test current values (e.g., $i_1$, $i_2$, and $i_3$) in Equation 1 use the absolute value of the current. The first test current value $i_1$ and the second test current value $i_2$ can each be defined by an average or summation of one or more predetermined test current values that occur during the third time interval $t_3$. The term $i_2$ is a second current value that is based on a fourth current value $i_4$, a fifth current value $i_5$, and a sixth current value $i_6$ measured during a third time interval. The third test current value $i_3$ can be defined by an average or summation of one or more predetermined test current values that occur during the second time interval $t_2$. One skilled in the art will appreciate that names "first," "second," and "third" are chosen for convenience and do not necessarily reflect the order in which the current values are calculated. A derivation of Eq. 1 can be found in U.S. Pat. No. 7,749,371, patented Jul. 6, 2010, which was filed on 30 Sep. 2005 and entitled "Method and Apparatus for Rapid Electrochemical Analysis," which is hereby incorporated by reference in its entirety into this application and attached hereto as part of the Appendix.

Referring now to FIGS. 7A and 7B, the peak current (FIG. 7B) observed at the end of $t_1$ and the beginning of the second test potential time interval $t_2$ (FIG. 7A) may be denoted as $i_{pb}$, and the peak current exhibited at the start of the third test potential time interval $t_3$ (FIG. 7A) may be denoted as $i_{pc}$. Equation 2 describes a relationship between the first current transient CT and second current transient CT when a test strip 62 is tested with a sample containing an interferent and no glucose.

$$i_{pc} - 2i_{pb} = -i_{ss} \qquad \text{Eq. 2}$$

In the case where there is no glucose in the sample, it is believed that the reagent layer 72 does not generate substantial amount of reduced mediator. Therefore, the current transients would reflect only the oxidation of interferents. At the early time scale regime of around 1.0 seconds, it is assumed that reagent layer 72 does not generate a significant amount of reduced mediator because of the glucose reaction. Further, it is assumed that the reduced mediator which is generated will mostly remain near first electrode 66, where reagent layer 72 was initially deposited, and not significantly diffuse to second electrode 64. Therefore, the magnitude of $i_{pb}$ is predominantly ascribed to interferent oxidation at second electrode 64 which is a direct interferent current.

At a duration after the third voltage E3 has been provided to the strip (e.g., about −300 mV) at around 4.1 seconds, reagent layer 72 does generate a significant amount of reduced mediator at first electrode 66 in the presence of glucose because of the glucose reaction. A significant amount of reduced mediator can also be generated because of a possible oxidation of an interferent with the oxidized mediator. As mentioned earlier, interferent that reduces oxidized mediator contributes to a current which may be referred to as an indirect current. In addition, interferents can also be oxidized directly at first electrode 66 which may be referred to as a direct current. For the situation in which the mediator can be oxidized at the working electrode, it may be assumed that the sum of the direct oxidation and indirect oxidation is approximately equal to a direct oxidation current that would have been measured if there was no oxidized mediator disposed on the working electrode. In summary, the magnitude of the $i_{pc}$ ascribed to both indirect and direct interferent oxidation, and the glucose reaction at the first electrode 66. Because it has been determined that $i_{pb}$ is controlled mainly by interferents, $i_{pc}$ can be used with $i_{pb}$ together to determine a correction factor. For example, as shown below $i_{pb}$ can be used with $i_{pc}$ in a mathematical function to determine a corrected current $i_{2(Corr)}$ which is proportional to glucose and less sensitive to interferents:

$$i_{2(CORR)} = i_2 \left[ \frac{|i_{pc}| - |2i_{pb}| + |i_{ss}|}{|i_{pc}| + |i_{ss}|} \right] \qquad \text{Eq. 3}$$

In exemplary step 612, $i_{pb}$ is measured after the start of the second test potential time interval $t_2$ and $i_{pc}$ is measured at the start of the third test potential time interval $t_3$. Applicants note that $i_{pc}$ may be the test current value at about 4.1 seconds, and $i_{pb}$ may be the test current value at about 1.1 second, based on the test voltage and test current waveforms in FIGS. 7A and 7B.

Eq. 3 was empirically derived to calculate a current $i_2$ $_{(Corr)}$ which is proportional to glucose and has a relative fraction of current removed that is ascribed to interferents. The term $i_{ss}$ was added to both the numerator and denominator to allow the numerator to approach zero when no glucose is present. Determination of the steady-state current $i_{ss}$ following application of the second electric potential is detailed in co-pending patent application Ser. No. 11/278,341, which is incorporated by reference into this application herein and attached hereto as part of the Appendix. Some examples of methods for calculating $i_{ss}$ can be found in U.S. Pat. Nos. 5,942,102 and 6,413,410, each of which is hereby incorporated by reference in its entirety and attached hereto as part of the Appendix.

In exemplary step 612, $i_{ss}$ is estimated by multiplying the test current value at about 5 seconds with a constant $K_8$ (e.g., 0.678). Thus, $i_{ss}$ can be approximated as $i(5) \times K_8$. The term $K_8$ can be estimated using Equation 4 where the number 0.975 is about the time in seconds after the third test voltage E3 is applied that corresponds to the current at approximately 5 seconds for the particular embodiment of the strip 62, which, assuming a linear variation over the time between about 0.95 seconds and 1 second, is the average current between 0.95 and 1 second, the term D is assumed to be about $5 \times 10^{-6}$ cm$^2$/sec as a typical diffusion coefficient in blood, and the term L is assumed to be about 0.0095 cm, which represents the height of the spacer 60:

$$i_{ss} = \frac{i(5)}{1 + 4\exp\left(\frac{-4\pi^2 D \times 0.975}{L^2}\right)} \qquad \text{Eq. 4}$$

Hence, a first blood glucose concentration G can be determined by Equation 5 that utilizes current $i_2$ $_{(Corr)}$, (which is proportional to glucose and has a relative fraction of current removed that is ascribed to interferents):

$$G = \left(\frac{|i_r|}{|i_l|}\right)^p (a|i_{2CORR}| - zgr); \qquad \text{Eq. 5}$$

where: $i_r = \sum_{t=4.4}^{t=5} i(t);$ $i_l = \sum_{t=1.4}^{t=4} i(t);$ $$i_{2(Corr)} = \left(\frac{|i_{pc}| + b|i_{ss}| - c|i_{pb}|}{|i_{pc}| + b|i_{ss}|}\right) i_r; \qquad \text{Eq. 5.1}$$

and

Where a, b, c, p, and zgr are glucose calculation coefficients.

Although the applied voltages are given as positive values in the preferred embodiments, the same voltages in the negative domain could also be utilized to accomplish the intended purpose of the claimed invention.

In this exemplary embodiment, $i_{pb}$ is the current measured at approximately 1.1 second; $i_{pc}$ is current measured from the electrodes of the strip 62 at approximately 4.1 seconds; $i_{ss}$ is the current measured at approximately 5 seconds. For ease of notation, Eq. 5.1 for this known glucose concentration calculation, can be represented in the following notation as Equation 5.2:

$$i_{2(Corr)} = \left( \frac{|i_{4.1}| + b|i_5| - c|i_{1.1}|}{|i_{4.1}| + b|i_5|} \right) i_r \qquad \text{Eq. 5.2}$$

It has been discovered by us that while the results from Equations 5 and 5.2 are satisfactory, the results could be improved for subjects whose hematocrits may encompass a wider range (20%-70%) as compared to the range of the typical subjects (40%-65%) such as those of neonates. We have therefore discovered a technique that allows us to acquire a more precise and accurate glucose result for subjects in this broad range. Furthermore, we have also devised a technique to allow for greater accuracy and precision in measuring neonates' blood glucose than as presently known. Finally, we have devised new calculation coefficients that give greater accuracy and precision for typical subjects whose hematocrits are within a predefined range.

Figure 8:
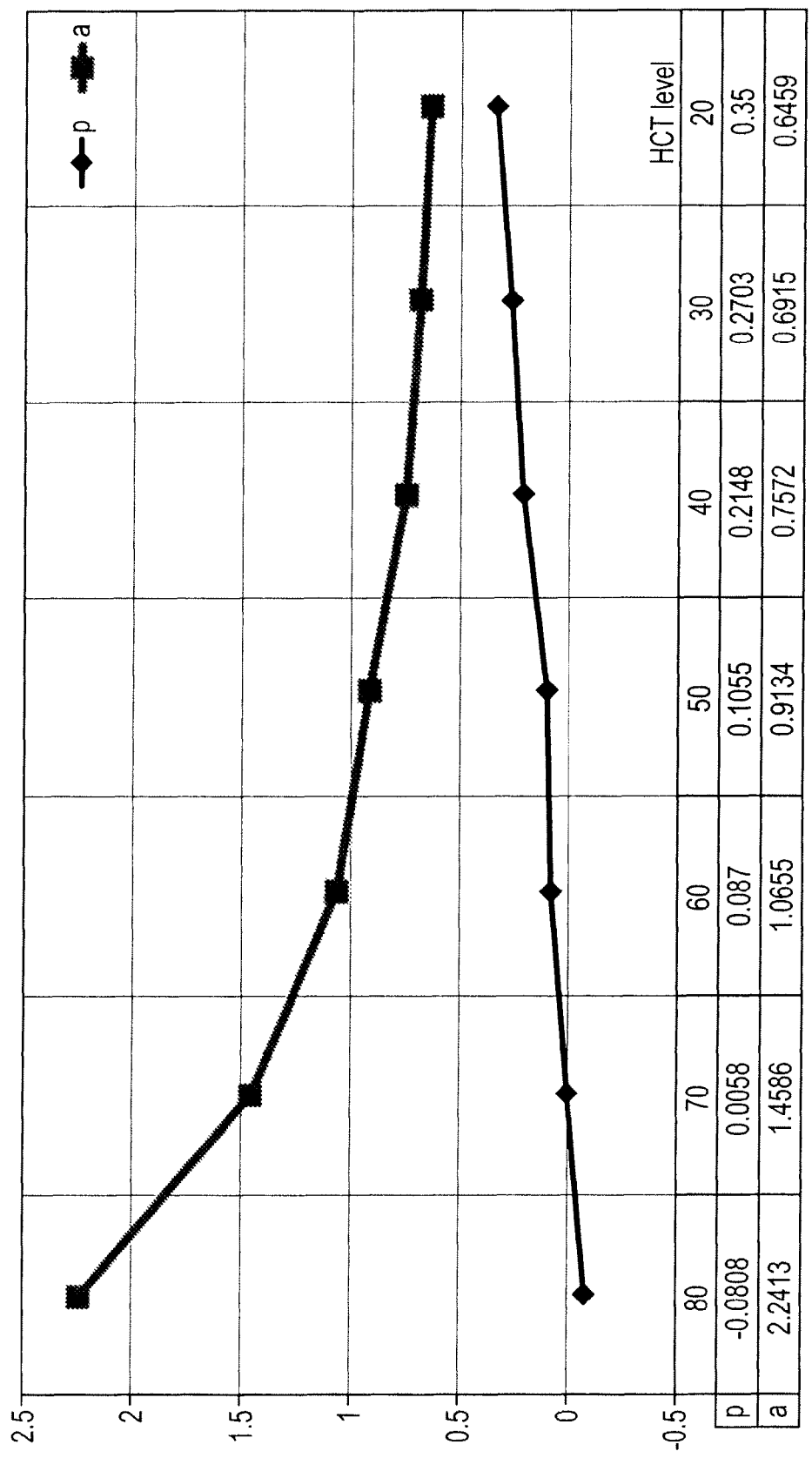
FIG. 8 illustrates the coefficients as a function of the hematocrit level.

In particular, the relevant coefficients in Equation 5 are "a"; "b"; and "zgr", were further refined iteratively such that the coefficients are a function of hematocrit values or defined ranges of hematocrits. This relationship between hematocrits and the coefficients is shown in FIG. 8. In FIG. 8, the non-dimensional value (vertical axis) of coefficients "p" and "a" were configured over specific hematocrit values, from 20% to 80% (horizontal axis) over interval of 10% so that the bias (i.e., the difference between calculated and referential glucose results), shown here in Table 1, are within acceptable ranges. In other words, from knowing the at least one physical characteristic (hematocrit) of the sample, applicants were able to derive glucose calculation coefficients from Table 1 that allowed the calculated glucose results to be much closer to referential glucose results, thereby reducing the bias between the referential glucose values and the corresponding glucose value calculated using this technique. Due to the rarity of actual blood samples with extreme ranges of hematocrits (i.e., at less than 45% hematocrits and greater than 60% hematocrits), actual referential blood samples were not utilized as part of applicants' experiments in deriving the revised coefficients. Instead, the referential glucose results were obtained from mathematical models of blood samples at various hematocrits, and which model had been validated against actual blood samples at different values of hematocrits. Because of the validations against actual blood samples and actual glucose results, applicants are confident that the model used to generate the referential glucose data correlates extremely well with actual samples and that these results using the revised coefficients would also reflect the improved accuracy and precision in actual glucose measurements through the entire range of hematocrits from about 20% to about 80%.

TABLE 1

Revised Coefficients As a Function of Hematocrit and Bias

| HCT, % | Referential Gref | Results G1 from Known Coefficients | Revised coefficient p | Revised coefficient a | Revised analyte G Result Based on HCT: | Bias: Gref − G1 | Bias: Gref − G |
|---|---|---|---|---|---|---|---|
| 20 | 100 | 153.3 | 0.3500 | 0.6459 | 91.18 | −53.3 | 8.82 |
|    | 150 | 241.9 | (zgr = 1.95) |    | 140.1 | −91.9 | 9.9 |
|    | 200 | 326.7 |    |    | 186.4 | −126.7 | 13.6 |
|    | 250 | 406.1 |    |    | 229.5 | −156.1 | 20.5 |
|    | 300 | 476.1 |    |    | 267.4 | −176.1 | 32.6 |
| 30 | 100 | 157 | 0.2703 | 0.6915 | 91.7 | −57 | 8.3 |
|    | 150 | 250.5 | (zgr = 1.9522) |    | 140.7 | −100.5 | 9.3 |
|    | 200 | 342.9 |    |    | 188.1 | −142.9 | 11.9 |
|    | 250 | 424.7 |    |    | 229.9 | −174.7 | 20.1 |
|    | 300 | 501.9 |    |    | 269.1 | −201.9 | 30.9 |
| 40 | 100 | 163.1 | 0.2148 | 0.7572 | 93.0 | −63.1 | 7 |
|    | 150 | 258.5 | (zgr = 1.96) |    | 139.9 | −108.5 | 10.1 |
|    | 200 | 358.8 |    |    | 186.9 | −158.8 | 13.1 |
|    | 250 | 456.4 |    |    | 230.7 | −206.4 | 19.3 |
|    | 300 | 555.5 |    |    | 274.1 | −255.5 | 25.9 |
| 50 | 100 | 164.8 | 0.1055 | 0.9134 | 92.2 | −64.8 | 7.8 |
|    | 150 | 269.3 | (zgr = 1.96) |    | 139.8 | −119.3 | 10.2 |
|    | 200 | 381.1 |    |    | 184.7 | −181.1 | 15.3 |
|    | 250 | 493.9 |    |    | 228.9 | −243.9 | 21.1 |
|    | 300 | 589.9 |    |    | 272.8 | −289.9 | 27.2 |
| 60 | 100 | 162.6 | 0.087 | 1.0655 | 93.9 | −62.6 | 6.1 |
|    | 150 | 266.5 | (zgr = 2.02) |    | 139.2 | −116.5 | 10.8 |
|    | 200 | 384.8 |    |    | 186.5 | −184.8 | 13.5 |
|    | 250 | 508.3 |    |    | 233.6 | −258.3 | 16.4 |
|    | 300 | 635.5 |    |    | 279.7 | −335.5 | 20.3 |
| 70 | 100 | 151.2 | 0.0058 | 1.4586 | 94.0 | −51.2 | 6 |
|    | 150 | 271.6 | (zgr = 1.97) |    | 141.0 | −121.6 | 9 |
|    | 200 | 406.6 |    |    | 187.5 | −206.6 | 12.5 |
|    | 250 | 550.2 |    |    | 233.0 | −300.2 | 17 |
|    | 300 | 704.1 |    |    | 278.1 | −404.1 | 21.9 |

TABLE 1-continued

Revised Coefficients As a Function of Hematocrit and Bias

| HCT, % | Referential Gref | Results G1 from Known Coefficients | Revised coefficient p | Revised coefficient a | Revised analyte G Result Based on HCT: | Bias: Gref − G1 | Bias: Gref − G |
|---|---|---|---|---|---|---|---|
| 80 | 100 | 129.5 | −0.0809 | 2.2413 | 96.0 | −29.5 | 4 |
|  | 150 | 235.2 | (zgr = 2.2413) |  | 139.9 | −85.2 | 10.1 |
|  | 200 | 373.4 |  |  | 183.3 | −173.4 | 16.7 |
|  | 250 | 539.3 |  |  | 228.9 | −289.3 | 21.1 |
|  | 300 | 784.1 |  |  | 287.2 | −484.1 | 12.8 |

Referring back to FIG. 6A, at step 614, the system may obtain from a look-up table (similar to Table 1) the revised coefficients based on the hematocrit determined from step 608. Once the "revised" coefficients are obtained from step 614, the logic utilizes these revised coefficients in the calculating step 616, which may use Equations 5 and 5.2 to arrive at the glucose concentration of the sample. At step 618, the logic may annunciate the result with a display, via audio or a suitable communication medium.

As noted earlier with regard to FIG. 6B, where the glucose measurement system does not include a provision to sense hematocrit directly, applicants have devised a technique in which to obtain a range of hematocrits once the age of a particular group of subjects, which in this case are neonates, is known. Neonates are believed to have much different hematocrit ranges than older subjects and whose hematocrit ranges are strongly related to the age of the neonates. Consequently, for the neonatal population, it is believed that age of the neonates (within a strictly defined upper threshold) can reliably be used to estimate hematocrit in such pediatric subjects. This is known generally and also described at: http://www.healthcare.uiowa.edu/path_handbook/Appendix/Heme/PEDIATRIC_NORMALS.html,
where it is shown that the hematocrit ranges correlate to the age of the neonates after birth up to six months. For clarity, the values for hematocrits in this referenced document are provided in Table 2.

TABLE 2

HEMATOLOGY: REFERENCE RANGES FOR THE NEONATAL BLOOD HEMATOLOGY

| TEST | AGE, MONTHS | RANGE | UNITS |
|---|---|---|---|
| HEMATOCRIT | 0-1 | 42-65 | % |
|  | 1-2 | 33-65 |  |
|  | 2-3 | 26-41 |  |
|  | 3-6 | 29-41 |  |
|  | 6-12 | 31-41 |  |

Figure 9:
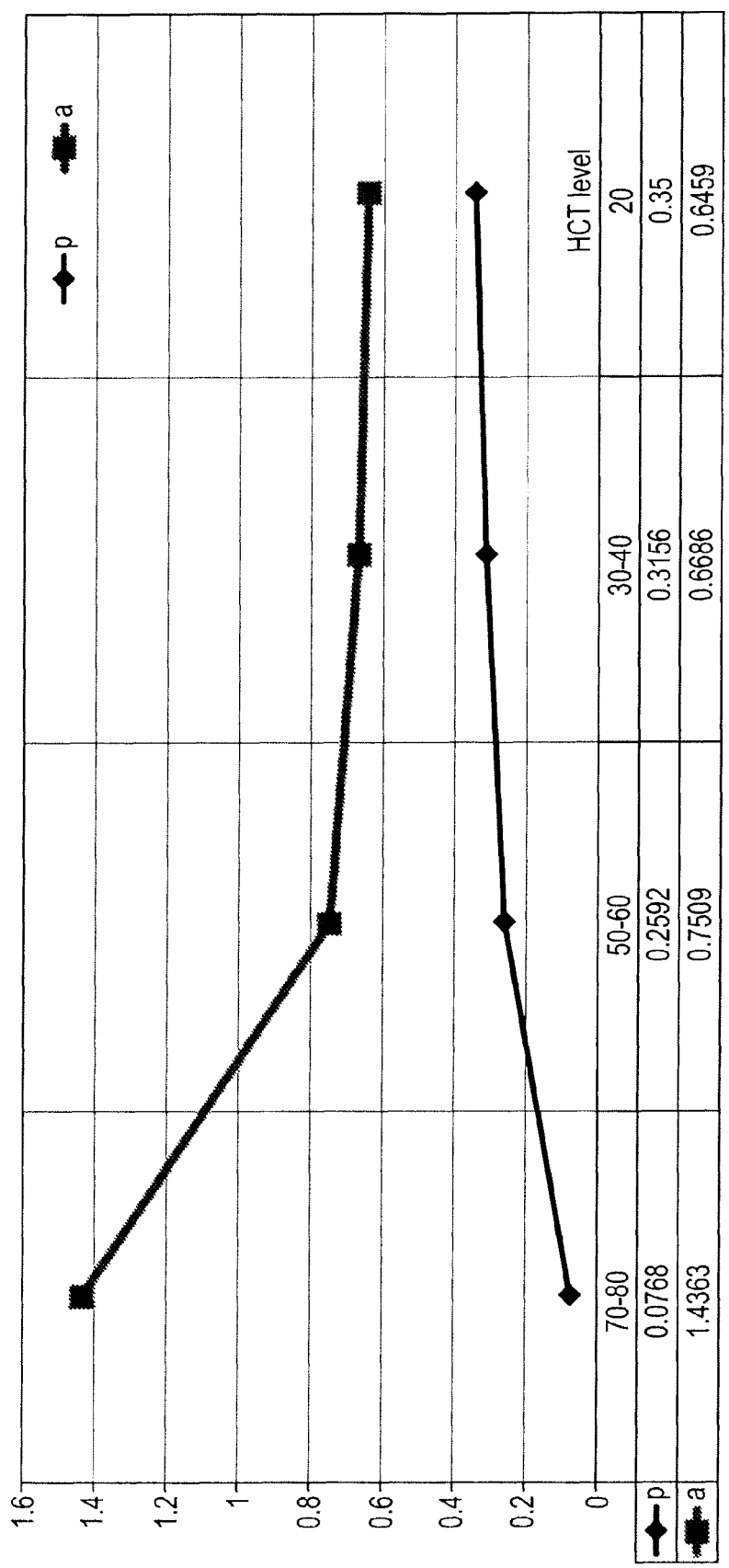
FIG. 9 illustrates the coefficients as a function of discrete ranges of hematocrits.

In the study of J. Jopling, E. Henry, S. Wiedmeier, *Reference Ranges for Hematocrit and Blood Hemoglobin Concentration During the Neonatal period: Data from a Multihospital Health Care System.* Pediatrics, Vol 123, N. 2, February 2009, pp. 333-337 (which is incorporated by reference with a copy attached to the Appendix and hereafter referred to as "the Jopling Study"), the study has shown that hematocrits are within the ranges noted in Table 2. In the same study, it was noted that there was an increase in hematocrits within four hours after birth for 32,534 patients, shown in FIG. 9A of the Jopling Study. Additionally, it can be seen (in FIG. 2, page e335) that hematocrit increases during the first 4 hours after delivery among late preterm and term neonates (gestational age 35-42 weeks) with a hematocrit increase of 3.6%. No change in hematocrit was observed during this period among the group of neonates 29 to 34 weeks' gestation, and a fall was seen in the group <29 weeks' (decrease in hematocrit of 6.0%). The mean values in this study are shown for hematocrit (with 32,534 patients) at delivery and during the first 4 hours after birth. Three groups of neonates are shown, according to gestational age (35-42 weeks, 29-34 weeks, and 22-28 weeks).

The same study has also shown that for 41,957 neonatal patients during the first 28 days of life, these patients had an approximately linear fall in hematocrit between the day of birth and day 28. Patients who were of 29 to 34 weeks' gestation began with lower hematocrit values that fell further (to 11 g/dL; 5%; 7.8 g/dL) by 28 days (shown here in FIGS. 8A-D on page e336 of the study). The few patients who were of less than 29 weeks of gestation had no erythrocyte transfusions such that reference ranges for the first 28 days could not be calculated reliably for that group.

Based on at least these two studies, applicants have devised a technique to determine the hematocrits of the neonate subject for step 608 with a look up table similar in form to Table 2 in order to derive a range of hematocrits for the subject.

Referring back to FIG. 6C, in this technique for neonates, the system, at step 608B', may ask the operator for the time and date of birth. The system may also ask for the condition of the neonate at birth (such as, for example, premature, late etc.) at step 608C'. At step 608D', the system estimate from the input data of step 608C' or 608D' to derive from Table 2 the hematocrit of the neonate subject.

Figure 10:
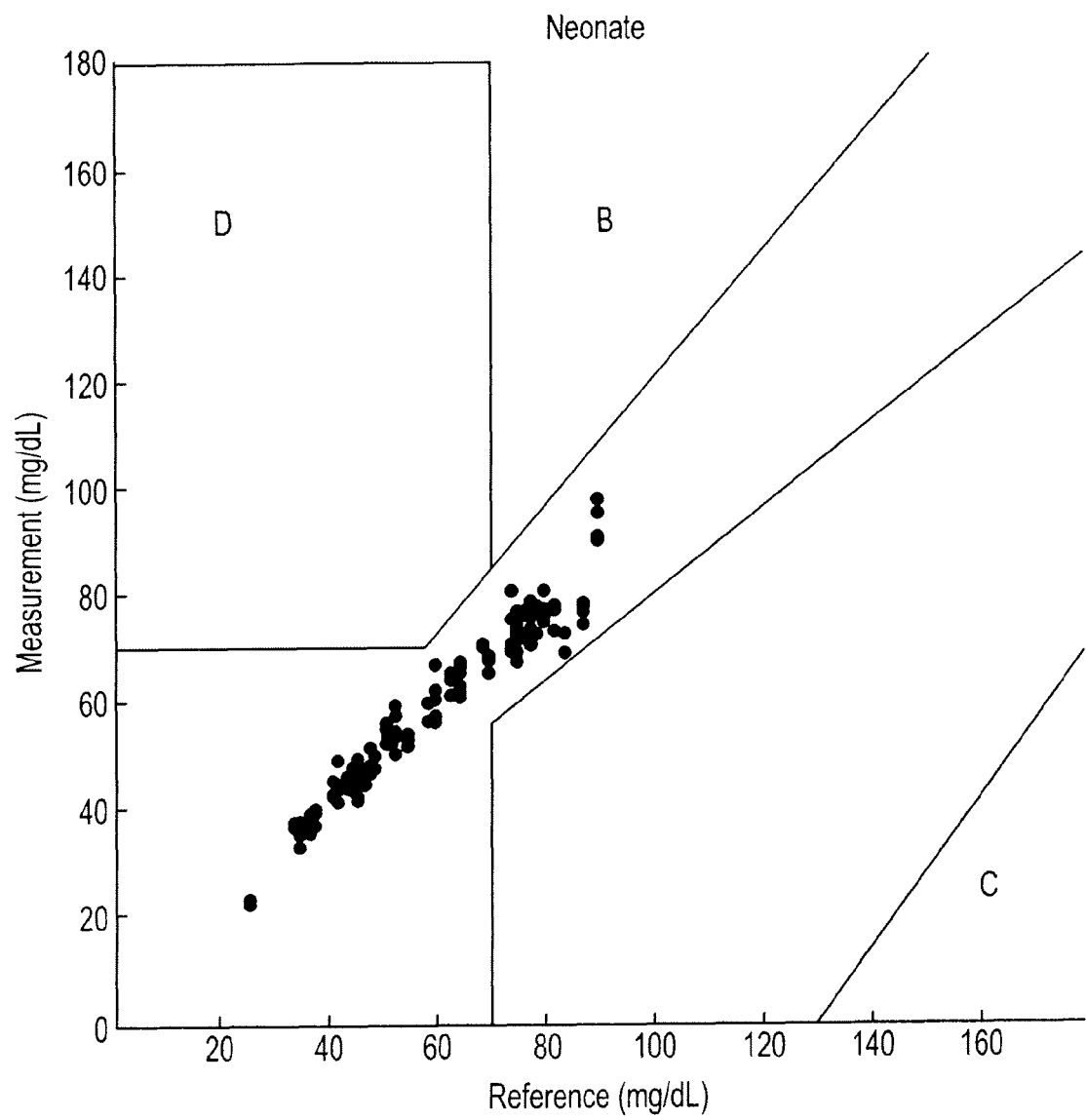
FIG. 10 illustrates the close correlation of measured glucose results with referential glucose results for neonate that are within acceptable accuracy level.

From a retrospective study, shown here in FIG. 10, it has been determined that for specific ranges of hematocrits of neonates, there are suitable coefficients that can be utilized in the calculation of glucose concentrations. Consequently, once the hematocrit range has been determined in step 608D', the system may look up revised coefficients in Table 3 below:

TABLE 3

REVISED ANALYTE COEFFICIENTS P AND A FOR THE EACH HCT RANGE

| HCT, % | Revised coefficient zgr | Revised coefficient p | Revised coefficient a |
|---|---|---|---|
| 30-40 | 1.5757 | 0.3156 | 0.6686 |
| 50-60 | 0.5530 | 0.2592 | 0.7509 |
| 70-80 | −1.2513 | 0.0768 | 1.3463 |

Figure 11:
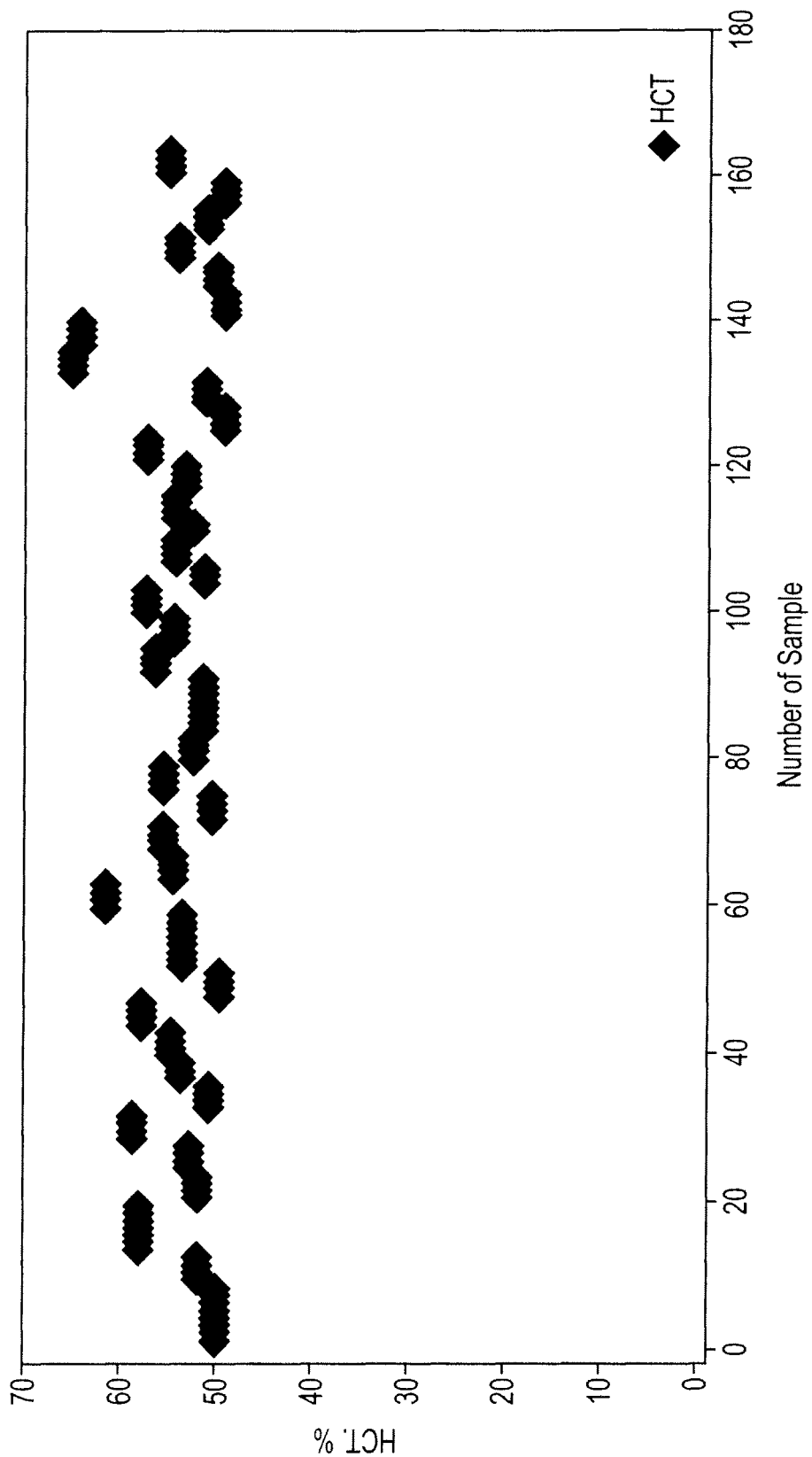
FIG. 11 illustrates the ranges of hematocrits for neonates across approximately 160 samples.

Once the revised coefficients "p", "a", and "zgr" have been determined for the neonate subjects from Table 3, the coefficients can then be utilized to calculate the glucose concentrations of such subjects from Equations 5 and 5.2.

Where the subjects involved are not neonates and where the system lacks the ability to detect hematocrit, it may be difficult to use appropriate calculation coefficients without a determination of hematocrits. In such instance, applicants have devised a technique that would be adequate to cover the range of hematocrits of typical subjects, which is believed to be in the range of 47% to 65%. Specifically, applicants conducted a retrospective analysis of and fitting of the data in FIGS. 10 and 11 to derive the calculation coefficients in Table 4 below:

TABLE 4

REVISED COEFFICIENTS TO HEMATOCRITS

| HCT, % | Revised analyte Coefficients | | |
|---|---|---|---|
|  | zgr | p | a |
| 47-65 | 4 | 0.433 | 0.171 |

Figure 12:
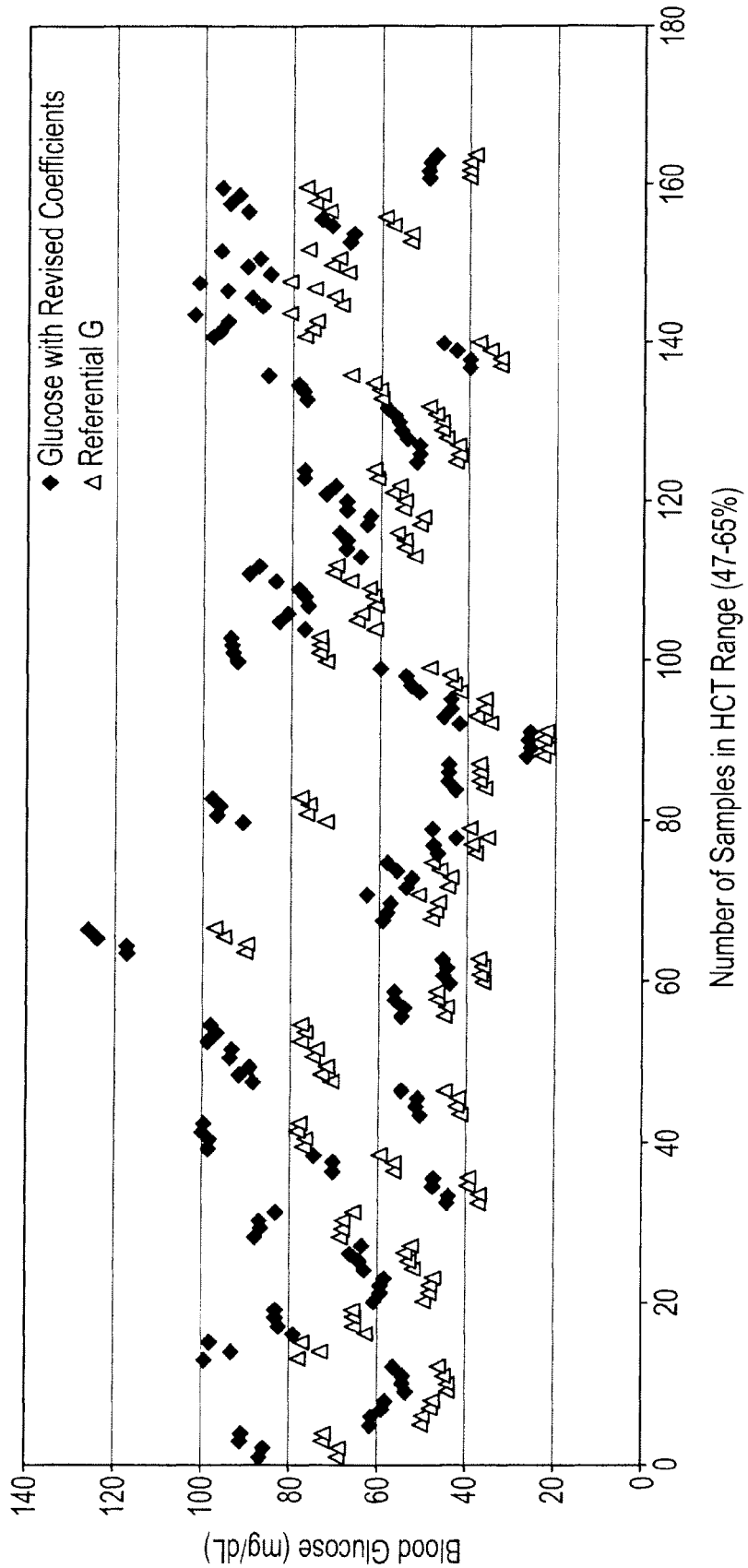
FIG. 12 illustrates the level of bias between referential glucose values as compared to measured glucose values using the revised coefficients of Table 4.

To validate these revised coefficients, bias is calculated and shown here in FIG. 12. When these coefficients were utilized, it was discovered that within the hematocrit range of 47%-65%, the bias between the referential glucose values as compared to the glucose values based on the revised coefficients showed a very good fit (i.e., relatively low bias for each referential glucose value).

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of determining blood glucose concentration with a glucose measurement system that includes a test strip and test meter, the test meter having a microcontroller configured to apply a plurality of test voltages to the test strip and measure a current transient output resulting from an electrochemical reaction in a test chamber of the test strip, the method comprising:
   inserting the test strip into a strip port connector of the test meter to connect at least two electrodes of the test strip to a strip measurement circuit;
   initiating a test sequence after deposition of a sample;
   determining at least one physical characteristic of the sample, the at least one physical characteristic being one of a hematocrit level, a viscosity, or a density of the sample;
   transforming analytes in the sample from one form to a different form;
   switching a first voltage to a second voltage different than the first voltage, the switching comprises changing the polarity of the second voltage with respect to the first voltage;
   measuring a first current output of the current transient from the at least two electrodes of the test strip after the changing from the first voltage to the second voltage;
   changing the second voltage to a third voltage different from the second voltage;
   measuring a second current output of the current transient from the at least two electrodes of the test strip after the changing from the second voltage to the third voltage;
   estimating a current that approximates a steady state current output of the current transient after the third voltage is maintained at the at least two electrodes of the test strip, the estimated current being a third current output of the current transient;
   obtaining analyte calculation coefficients of the test chamber based on the at least one physical characteristic of the sample; and
   calculating the blood glucose concentration based on the first, second and third current outputs of the current transient and the analyte calculation coefficients.

2. The method of claim 1, in which the blood glucose concentration is obtained with an equation of the form:

$$G = \left(\frac{|i_r|}{|i_l|}\right)^p (a|i_{2CORR}| - zgr);$$

where: $G$ comprises the blood glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right) i_r$$

where:
a, p, and zgr are determined from the obtaining step;
b comprises approximately 0.205;
c comprises approximately 2;
$i_{4.1}$ comprises the first current output measured at approximately 4.1 seconds after initiation of test sequence;
$i_5$ comprises the third current output measured at approximately 5 seconds after initiation of test sequence; and
$i_{1.1}$ comprises the first current output measured at approximately 1.1 seconds after initiation of test sequence.

3. The method of claim 1, in which the determining of the at least one physical characteristic of the sample comprises:
   driving an alternating signal into the test chamber;
   measuring an impedance from an output signal of the test chamber; and
   correlating the impedance with the hematocrit level of the sample.

4. The method of claim 1, in which the determining of the at least one physical characteristic of the sample comprises:
   determining an age of the subject from birth to no more than one year old; and
   selecting the hematocrit level based on the age.

5. The method of one of claim 3 or claim 4, in which the obtaining comprises selecting from a look-up table having the analyte calculation coefficients for each level of hematocrit.

6. A method of determining blood glucose concentration with a glucose measurement system that includes a biosensor and test meter, the test meter having a microcontroller configured to apply a plurality of test voltages to at least two electrodes of the biosensor and measure a current transient output resulting from an electrochemical reaction in a test chamber of the biosensor, the method comprising:

initiating a test sequence after deposition of a sample;

transforming analytes in the sample from one form to a different form;

switching a first voltage to a second voltage different than the first voltage, the switching comprises changing the polarity of the second voltage with respect to the first voltage;

measuring a first current output of the current transient from the at least two electrodes after the changing from the first voltage to the second voltage;

changing the second voltage to a third voltage different from the second voltage;

measuring a second current output of the current transient from the at least two electrodes after the changing from the second voltage to the third voltage;

estimating an approximate steady state current output of the current transient after the third voltage is maintained at the at least two electrodes, the estimated approximated steady state current output being a third current output of the current transient;

calculating a blood glucose concentration based on the first, second and third current outputs of the current transient with an equation of the form:

$$G = \left(\frac{|i_r|}{|i_l|}\right)^p (a|i_{2CORR}| - zgr);$$

where: $G$ comprises the blood glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.1}|}{|i_{4.1}| + b|i_5|}\right) i_r$$

where:

a comprises approximately 0.171;

b comprises approximately 0.678;

c comprises approximately 2;

p comprises approximately 0.433;

zgr comprises approximately 4;

$i_{4.1}$ comprises the second current output measured at approximately 4.1 seconds after initiation of test sequence;

$i_5$ comprises the third current output measured at approximately 5 seconds after initiation of test sequence; and $i_{1.1}$ comprises the first current output measured at approximately 1.1 seconds after initiation of test sequence.

7. The method of claim 6, in which coefficients p, a, and zgr for samples with approximately 20% hematocrit comprise respectively, 0.35, 0.6459 and 1.95, the coefficients p, a, and zgr for samples with approximately 30% hematocrit comprise respectively 0.2703, 0.6915, and 1.9522, the coefficients p, a, and zgr for samples with approximately 40% hematocrit comprise respectively 0.2148, 0.7572, and 1.96; the coefficients p, a, and zgr for samples with approximately 50% hematocrit comprise respectively 0.1055, 0.9134 and 0.196; the coefficients p, a, and zgr for samples with approximately 60% hematocrit comprise respectively 0.087, 1.0655, and 2.02, the coefficients p, a, and zgr for samples with approximately 70% hematocrit comprise respectively 0.0058, 1.4586, and 1.97, the coefficients p, a, and zgr for samples with approximately 80% hematocrit comprise respectively −0.0809, 2.2413 and 2.2413.

8. The method of claim 6, in which coefficients p, a, and zgr for samples with hematocrits in a range of 30-40% hematocrit comprise respectively 0.3156, 0.6686 and 1.5757; the coefficients p, a, and zgr for samples with hematocrits in a range of 50-60% hematocrit comprise respectively 0.2592, 0.7509 and 0.5530; the coefficients p, a, and zgr for samples with hematocrits in a range of 70-80% hematocrit comprise respectively 0.0768, 1.3463 and −1.2513.

* * * * *